United States Patent [19]

Iwasaki et al.

[11] Patent Number: 5,525,806
[45] Date of Patent: Jun. 11, 1996

[54] FOCUSED CHARGED BEAM APPARATUS, AND ITS PROCESSING AND OBSERVATION METHOD

[75] Inventors: Koji Iwasaki; Tatsuya Adachi; Yutaka Ikku; Takashi Kaito, all of Tokyo, Japan

[73] Assignee: Seiko Instruments Inc., Tokyo, Japan

[21] Appl. No.: 191,863

[22] Filed: Feb. 4, 1994

[30] Foreign Application Priority Data

Feb. 5, 1993 [JP] Japan .................................. 5-019059

[51] Int. Cl.⁶ .............................. H01J 37/26; H01J 37/30
[52] U.S. Cl. .................... 250/492.21; 250/307; 250/310; 250/311
[58] Field of Search .................................... 250/306, 307, 250/309, 311, 492.21, 310

[56] References Cited

U.S. PATENT DOCUMENTS

| | | | |
|---|---|---|---|
| 4,219,731 | 8/1980 | Migitaka et al. | 250/397 |
| 5,023,453 | 6/1991 | Adachi et al. | 250/309 |
| 5,270,552 | 12/1993 | Ohnishi et al. | 250/309 |
| 5,331,161 | 7/1994 | Ohdomari et al. | 250/309 |

*Primary Examiner*—Bruce C. Anderson
*Attorney, Agent, or Firm*—Loeb & Loeb

[57] ABSTRACT

To process sample of specific portion or position for the transmission electron microscope [TEM] simply to the most suitable or optimal shape, and to confirm the sample thickness of the sample while processing above (on-going confirmation). To make TEM sample through etching by way of irradiation of ion beam 2 onto sample 4, and to confirm processing status of sample by way of irradiating electron beam 7 from horizontal angle to cross-section of sample, and of detecting secondary electron, reflection electron, X ray, and transmission electron with respective detector 5, 9, 10, and 11, and to estimate the thickness of sample in process above since the intensities of these signals above changes due to the thin film thickness of sample.

6 Claims, 5 Drawing Sheets

IMAGE BY REFLECTION ELECTRONS

IMAGE BY TRANSMISSION ELECTRONS

IMAGE BY X-RAYS EXITED TRANSMISSION SCATTERING ELECTRONS

IMAGE BY SECONDARY ELECTRONS

18 P Si WIRE

FOCUSED CHARGED BEAM APPARATUS, AND ITS PROCESSING AND OBSERVATION METHOD

BACKGROUND OF THE INVENTION

This invention relates to focused charged ion-beam apparatus. Its sample processing and its observation method for the above apparatus, which can observe the sample surface by way of detecting the secondary particles which in emitted (generated) from the said sample through the irradiation of the focused ion-beam, and which can process a transmitted area of the sample surface by way of ion-beam etching and ion-beam CVD processing, by way of which thin-film processing of the sample and the estimation of its thickness can be realized, and especially the processing of the most suitable thickness and this shape can be simply realized in TEM sample processing.

Traditional focused ion-beam apparatus in prior art is, as disclosed in Japanese official gazette under the volume of Unexamined Published Japanese Patent Application 59-168652, that which derives its ion-beam from the liquid metal ion source through the electrode, transform the ion beam above to the focused one by way of the aperture and the electrostatic lens and deflects and scans the focused ion-beam by way that the focused ion-beam irradiates a predetermined area of the sample surface through deflecting electrode.

Due to the repeated irradiation of the said scanned focused ion-beam on the sample surface 4, a predetermined area on the sample surface 4 are come off since it is spattered by ion-beam. And an ion-beam CVD metal film can be formed on the focused ion-beam irradiation area on the sample 4 by way of blasting through nozzle of the gas gun for deposit. These functions are utilized in the circuit amendment (correction) and/or process appreciation, of sample IC. By way of this utilization above, debug time in IC development. (Refer to "Monthly Semiconductor World", Vol. 1987.9.]

Recently, a case is reported that sample making of TEM cross-section is done by focused ion-beam apparatus and its observation result of cross-section TEM area on sample surface is also reported (The 37th Applied Physics Society 1990.3 "How to make (process) TEM Cross-section Sample by Focused Ion-beam"). According to this method, cross-section TEM (transmission electron microscope) sample making at a predetermined area can be done in short time compared to the traditional ion-milling method.

An embodiment of traditional focused ion-beam apparatus in prior art is shown in FIG. 3. Liquid metal ion source is used as for ion source 1. The ion-beam 2 which is derived from the ion source 1 irradiates the sample surface 4 by way of focused and scanned by ion optics systems 3. The ion-optics systems 3 is comprising of an aperture 30 which passes only optical axis of ion-beam 2 through, an electrostatic lens 31 which focuses ion-beam 2, a deflecting electrode 32 which deflects the optical axis 2 of focused ion-beam for the purpose of irradiation of the focused ion-beam on a predetermined area on the sample surface 4, a blanker 33 which controls on-off of irradiation of focused ion-beam 2 on sample surface 4, and etc.

The focused ion-beam 2 etches the sample surface 4 and discharges the secondary particle which is excited by ion-beam. The secondary electron in these secondary particle is detected by the secondary electron detector and is displayed on observation CRT which is not shown in the Figure, as SIM image. And at the same time with irradiation of ion-beam 2, CVD gas is supplied through the nozzle of gas gun 4, and therefore a thin-film is formed on the sample surface 4. This kind of ion-beam processing apparatus is traditionally utilized for cutting off or connection, processing of cross-section surface, or observation, of IC circuits.

When cross-section surface sample for TEM is made by way of apparatus in prior art above, the front and rear sides of observation area on the sample which is sliced mechanically towards several (some) 10 μm is removed through ion-beam etching, in order that a "wall" less than 0.5 μm in thickness is left. Next, observation of the processed shape or confirmation of cross-section surface of sample through image observation by scanning electron microscope (hereinunder abbreviated as SEM) in order to avoid the damage due to ion-beam irradiation and if necessary, processing is continued. Then the observation of after-process sample is made by TEM and ion-beam etching may be necessitated again in case that the processing above is not sufficient to observation. This method above takes much time for preparation of vacuous atmosphere or for sample position adjustment, etc., since a sample is put into and picked out of, several vacuum utilization devices, and has the difficulty in processing of the optimal cross-section surface of TEM sample.

SUMMARY OF THE INVENTION

In order to solve the above-specified problems, the focused ion-beam apparatus in this invention is characterized in having an irradiation systems which can irradiate electron beam on the sample from horizontal direction, and a detector which detects secondary signal which is excited by ion-beam (secondary electron, reflection electron, transmission electron, electron, and X ray).

Since ion-beam etching of testing sample surface in process can be done after the said scanning of focused ion-beam, and SIM image observation for processing and position adjustment of sample through detection of secondary electron excited by ion-beam, a thin-film making at specific area of testing sample, especially of cross-section surface sample for TEM can be made in this invention. And if necessary, observation, through SEM image, of processing status and estimation of thickness of such thin-film sample due to monitoring of reflection electron, transmission electron, and X-ray which is excited by scattered transmission electron, can be realized in using the said electron beam in exchange for the said ion-beam.

And by detecting the said electron or X-ray which is excited by the said electron-beam, element analysis at the micro position on the cross-section surface can be realized in non-destructive examination. Moreover, alleviation of roughly processed surface (TEM observation surface), which is irregularity on the sample surface, can be realized by way of protection from damage by ion-beam irradiation on the sample (work) surface due to the said ion-beam CVD which makes thin-film on a predetermined position of the observation surface of the sample (work) just before ion-beam etching is done, and makes its surface flat. The uniform thickness of thin wall of TEM observation surface can also be realized by way that the slope of processed cross-section surface which is spread due to the said focused ion-beam is kept at vertical position against the sample (work) surface itself which should be kept diagonal by several degree at the time of ion-beam etching. Therefore, in this invention, the optimal shape forming of sample (work), especially TEM sample, and thickness estimation of sample which processed to thin-film, can be easily realized.

DETAILED DESCRIPTION

Figure 1:
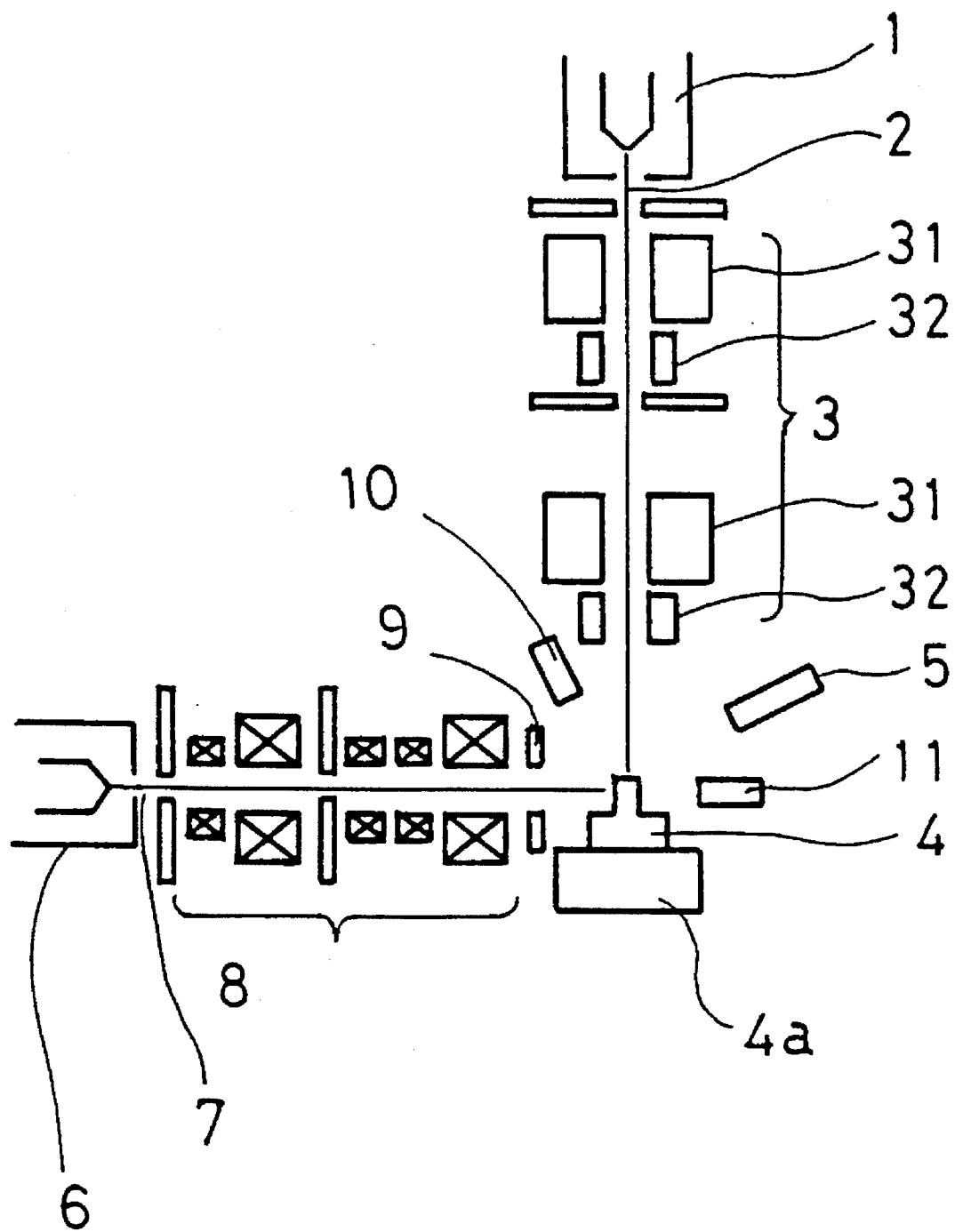
FIG. 1 shows the outline cross-section drawing of an embodiment in this invention.

Hereinafter embodiment is this invention is rendered in using Figures. FIG. 1 shows outline cross-section drawing of electron charged beam apparatus for cross-section surface process observation in this invention.

Liquid metal ion source is used for ion gun 1, by which ion beam 2 is derived. The ion beam 2 is turned to be focused ion-beam 2 through accelerating, focusing, and scanning by ion-optics systems. Then the focused ion-beam 2 is irradiated onto the sample 4 on 5 axis sample stage 4a. The secondary electron which is excited by ion-beam and which is discharged from sample 4, is detected by the secondary electron detector and its SIM (scanning ion microscope) image is displayed on CRT 13 (refer to FIG. 2), by which observation of sample 4 surface and positioning of processed sample (work) become possible. And then thin-film formation on sample by way of spattering due to irradiation of focused ion-beam 2, especially sample making for TEM observation can become possible.

Irradiation systems of electron-beam 7 is structured in the position where it is at right angle (exactly 90 degree) in contrast to the irradiation systems of focused ion-beam 2. Next, by stopping the focused ion-beam 2 irradiation onto sample 4, the irradiation of electron-beam 7 is initiated onto the sample 4, instead. The electron beam 7 which is derived from electron gun 6 is accelerated, focused, and scanned by electron lens system 8, and irradiated onto the above sample 4. The secondary electron and X ray which are excited by electron beam and discharged from sample 4 detected respectively by the secondary electron detector 5 and X ray detector 10. And reflection electron and transmission electron are detected respectively by reflection electron detector 9 and transmission electron detector 11. Since these detected signals are changed in its intensity in relation to sample thickness, approximate thickness of sample in thin-film processing can be estimated by way that the relation between sample thickness and signal intensity should beforehand be acquired through real measurement and calculation. Since the sample thickness of thin-film processing and thin-filmed sample can be estimated in this invention, specific position or specific area on TEM sample can be processed to be in optimal or the most suitable thickness.

Figure 2:
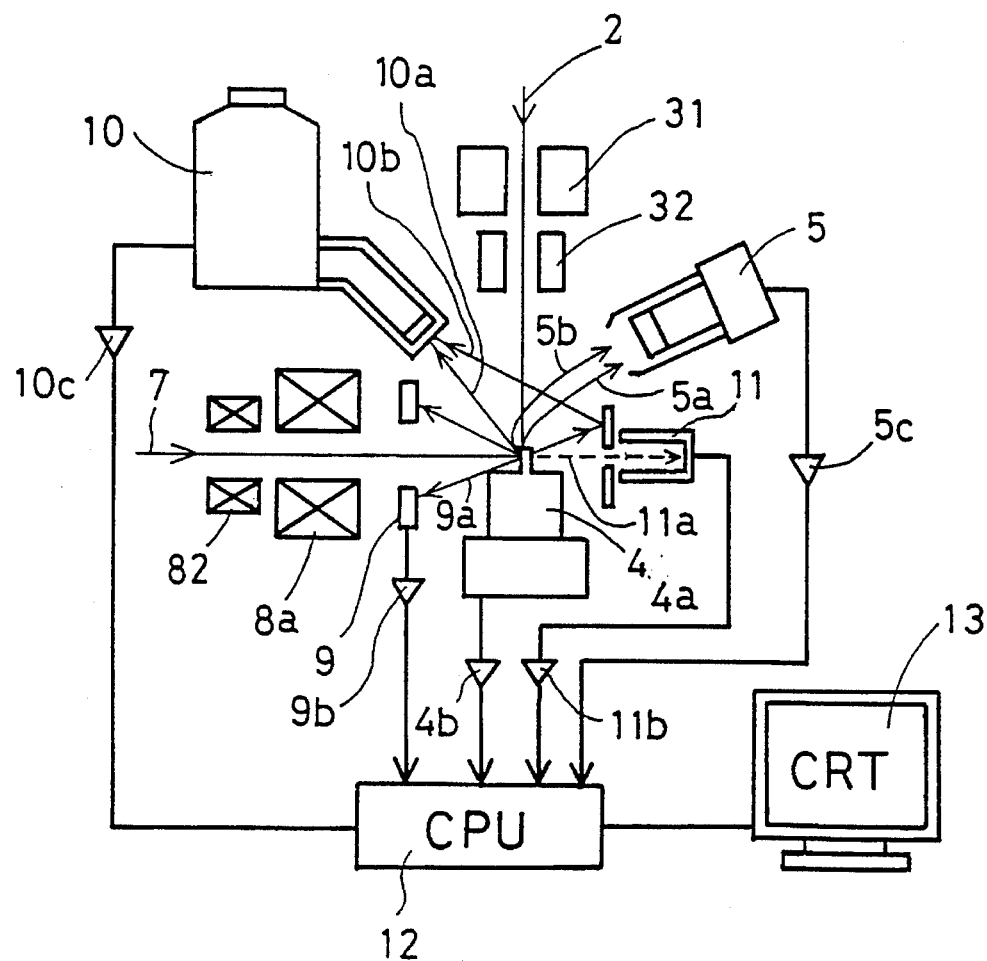
FIG. 2 shows the magnified cross-section drawing of sample periphery in this invention.
Figure 3:
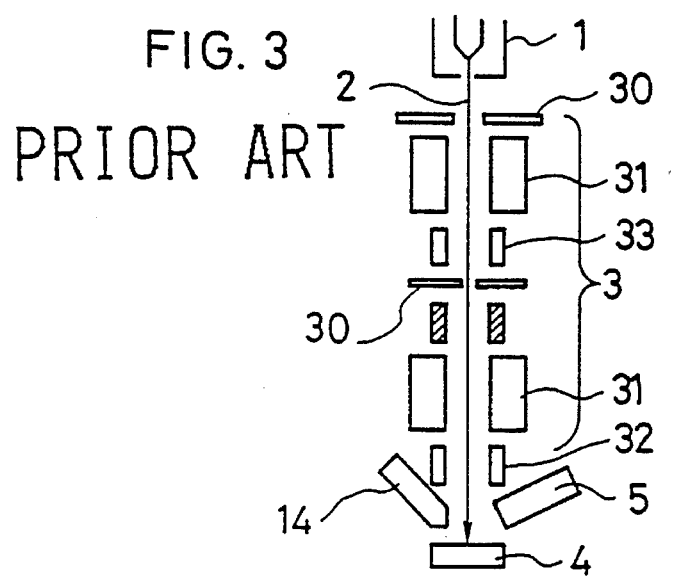
FIG. 3 shows the outline cross-section drawing of an embodiment in prior art.

FIG. 2 shows a magnified drawing of sample and its periphery of the apparatus in this invention. The focused ion-become 2 and electron-beam 7 which are scanned by scanning electrode 32 in ion-optics systems and by scanning coil 82 are alternatively irradiated onto sample 4 and secondary electron 5a, 5b which are excited by ion and electron are detected by secondary electron detector 5. Such secondary electron signal 5a, 5b which are detected as above are amplified by amplifier (for secondary electron) 5c and are input into process computer (CPU) 12, and then displayed on display CRT 13 respectively as SIM image and SEM image. By way of these images, confirmation of processing position, shape processed, and cross-section surface processed, of sample can be realized.

Reflection electron 9a which is reflected due to irradiation of electron beam 7 on sample surface which is TEM sample observation surface make by spatter-etching by irradiation of focused ion beam 2 is detected by electron detector 9. Reflection electron signal detected above is amplified by amplifier 9b and is input into CPU 12, then displayed onto CRT 13 as reflection electron.

X ray 10a, which is directly excited by irradiated electron beam 7 on and is discharged from sample surface, and X ray 10b, which electron that transmitted thin-film processed position of the sample and is scattered, emitted by excitation of sample of which portion is other than the observation surface of sample, are detected by X ray detector 10. X ray signal as such detected above is amplified by amplifier 10c and is input into CPU 12 and displayed on CRT 13 as X ray image. Moreover, electron beam 11a which is irradiated by electron beam 7 and transmitted sample 4 almost without being scattered is detected by transmission electron detector 11. Transmission electron signal as such detected above is amplified by amplifier 11b and is input into CPU 12 and then is displayed on CRT 13 as transmission electron image. Absorbed electric current which is the current that irradiated electron beam 7 is absorbed into sample 4 as current is amplified by amplifier 4b and is input into CPU 12 and is displayed on CRT 13 as absorbed electric current.

Since thickness of sample (work) in process can be estimated by monitoring the intensity of these signals, optimization of thickness of TEM sample can be realized. Moreover, since reflection electron, transmission electron and X ray which are all excited by electron beam are different in the characteristics from secondary electron, observation of reflection electron image, transmission electron image and X ray image which are originated in electron beam excitation due to the irradiation of electron beam 7 can be done even when the focused ion beam 2 is irradiated. That is, while TEM sample is processed in making through spattering and etching by ion beam irradiation, the thickness of sample can be confirmed by monitoring of reflection electron, transmission electron and electron-excited X ray which are emitted by electron beam excitation by its simultaneous irradiation with that of ion beam.

FIG. 6 shows a drawing which is for explanation of an embodiment of processing method in this invention. The surface layer which includes observation purpose area of semiconductor circuit (IC) sample (device-formed area), which is sample 4 for TEM observation of cross-section surface, is polished mechanically to the shape as shown in FIG. 6(a).

Semiconductor circuit on sample 4 is sliced by the width of 0.5 to 1 mm and then device portion which is formed on the sample surface 4a is polished at the depth of 50 to 100 μm and as a result, the rear side of it is eliminated which is the rest portion under the device surface of which depth is up to 100 μm.

Next, secondary electron which originated due to focused ion beam 2 irradiation is detected by secondary electron detector 5 and observed through SIM image, by means of irradiating the said focused ion beam 2, while scanning, onto the surface 4a of sample 4 by way of the focused ion beam irradiation systems. The observation image above is, for example, shown in FIG. 6(b). Then the position to observe a (cross) section 22 is to be decided through SIM observation image above. The position to observe a (cross) section 22 in this embodiment is a cross-section of contact hole 19. A broad local area which includes contact hole portion 19 where observation position 22 is in is determined and which is local area of a formed film 20 for CVD metal film 23 (film formed by ion beam and CVD), then metal film 23 is formed on the area, by alternate repetitions spraying of CVD gas (metal organic compound fog) by gas gun (which is not shown) and of irradiation of the focused ion beam 2 on the inside of local area of a formed film, this metal film 23 has an effect that the damage of the sample surface 4a due to irradiation of focused ion-beam 2 is alleviated.

Figure 6A:
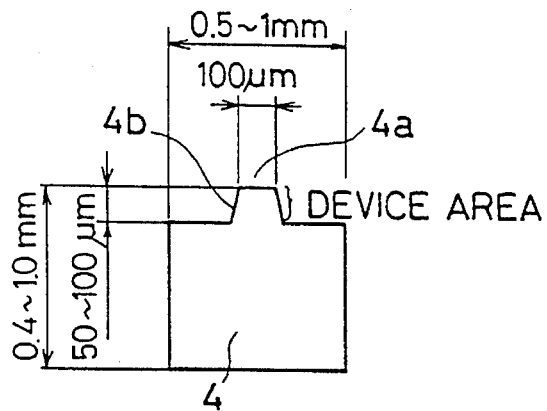
FIGS. 6A–F show a plan view drawing which exhibits sample processing method.
Figure 6B:
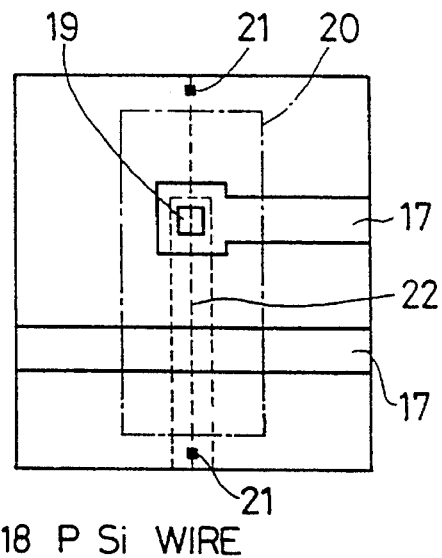
Figure 6C:
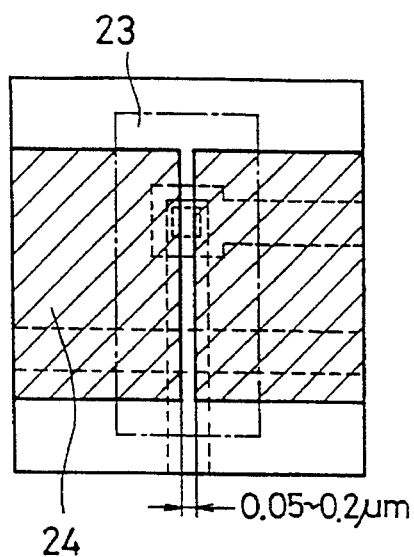
Figure 6D:
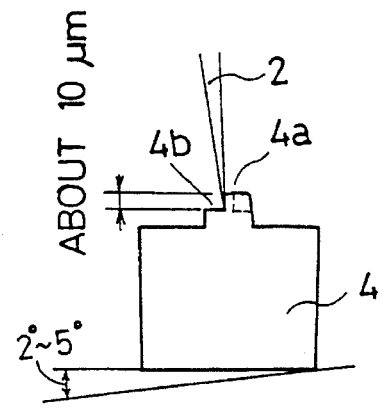

At this moment, a mark 21 is put on both sides of cross-section observation position 22 by through-hole processing by way of etching due to focused ion beam irradiation 2, by which holes observation position is easily found and processing can be done precisely. And then as shown in FIG. 6(c), the center portion of contact hole 19 except for the width of 0.05 to 0.2 µm of its center is spattered and etched by focused ion beam 2 in order to eliminate etching area 24, by the depth of about 10 µm, of both (left and right) sides of the center to be left as it is.

Figure 5A:
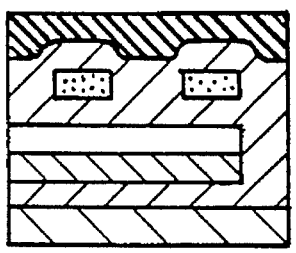
FIGS. 5A–D show observation images in order to explain the samples of observation images in this invention.
Figure 5B:
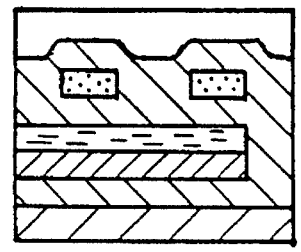
Figure 5C:
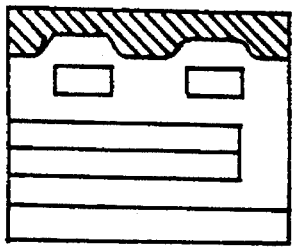
Figure 5D:
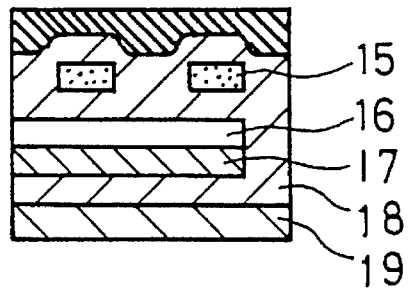
Figure 6E:
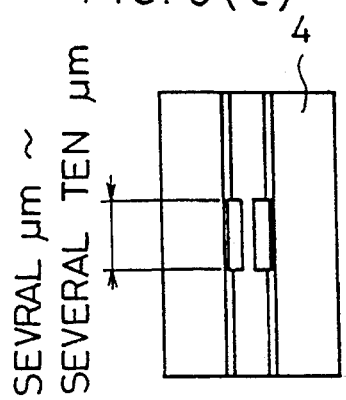
Figure 6F:
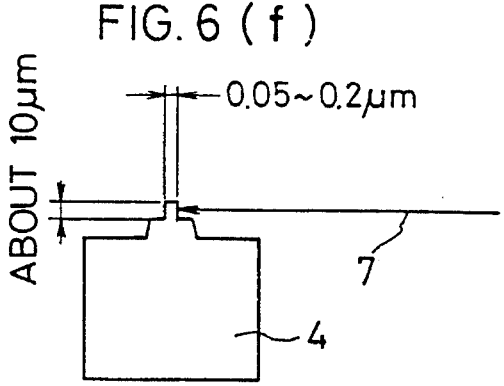

At this time, the slope of etched cross-section in relation to the focussing angle of focused ion beam is adjusted through leaning the sample 4 by several degrees (2 to 5 ○ is shown in FIG. 5(d) and then vertical thin film can be formed. And electron beam 7 is irradiated on the observation position in cross-section surface of device 4b on sample 4 through electron beam irradiation systems, transmission electron 11a is detected by transmission electron detector 11, it is confirmed if the intensity of transmission electron is sufficient enough. In case that the intensity above is small, irradiation of focused ion beam 2 is done again by way that etching area 24 in FIG. 6(c) locates closer to the position to observe a (cross) section 22. Electron beam is layout at the right angle against the optical axis of focused ion beam as shown in FIG. 1, and is vertically irradiated on the cross-section of sample 4. FIG. 6(e) and (f) are the shape of sample 4 respectively from upper side and from cross-section, after the processing.

Figure 4A:
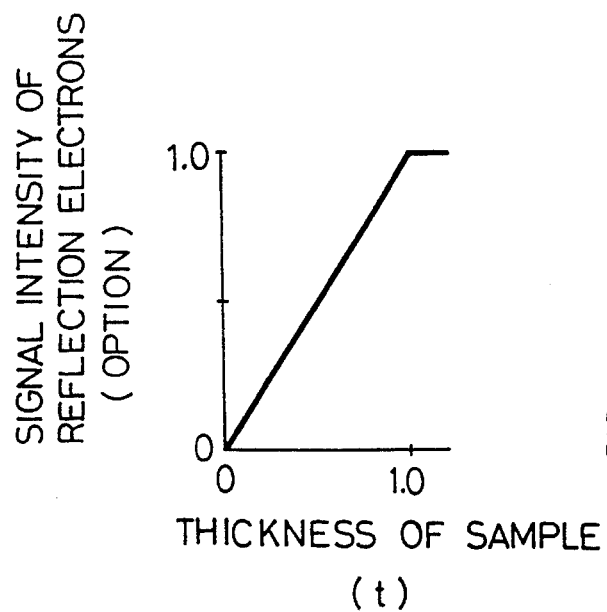
FIGS. 4A–C show the graph of the relation between sample thickness and specified secondary signals, which is for the explanation of the method in this invention.

FIG. 4 shows a drawing for the explanation of the sample thickness estimation method in this invention. FIG. 4(a) shows a simple drawing of the relation between sample thickness and intensity of reflection electron. Assume that the range of irradiated electron beam on sample and its intensity of the reflection electron signal are respectively 1 and 0, the intensity of reflection electron decreases in case that thickness of sample is thinner than the range of electron beam. Although the relation between thickness of sample and the intensity of reflection electron signal depends on sample element or crystalline substance, thickness of thin film sample can be estimated through measurement and/or calculation, beforehand, of intensity ratios of irradiated electron beam intensity against reflected electron intensity. This method above is the best for TEM sample arrangement which needs thin-film process, because this method is utilized for confirmation of thickness of sample in thin-film process through ion beam.

Figure 4B:
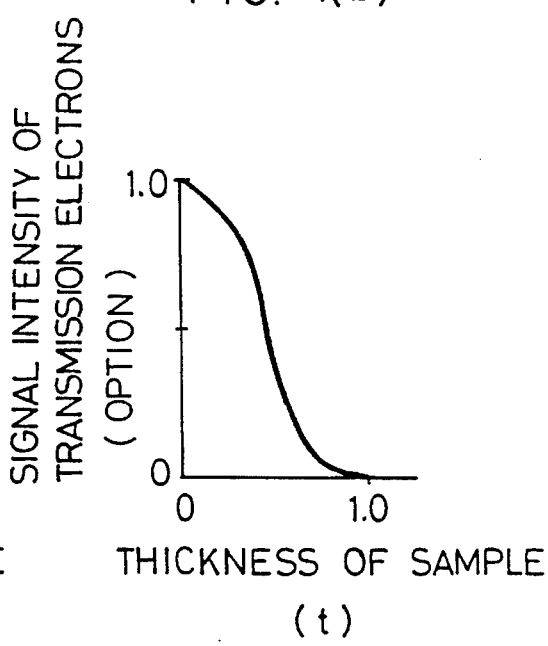

FIG. 4(b) exhibits the relation between thickness of sample and the transmission electron intensity. Suppose that the range of irradiated electron beam on sample and irradiated electron intensity are respectively 1 or 0, then the transmission electron density increases the more, when the thickness of sample becomes thinner than the range of electron beam. In case the thickness of sample is not thinner enough, since almost all transmission electrons become scattered transmission electron, the number of that which transmission electron is detected by transmission electron detector is rather fewer.

In case that thickness of sample becomes thinner enough, almost all of transmission electron can be detected by the transmission electron detector. This is why the relation is drawn like the FIG. 4(b).

Figure 4C:
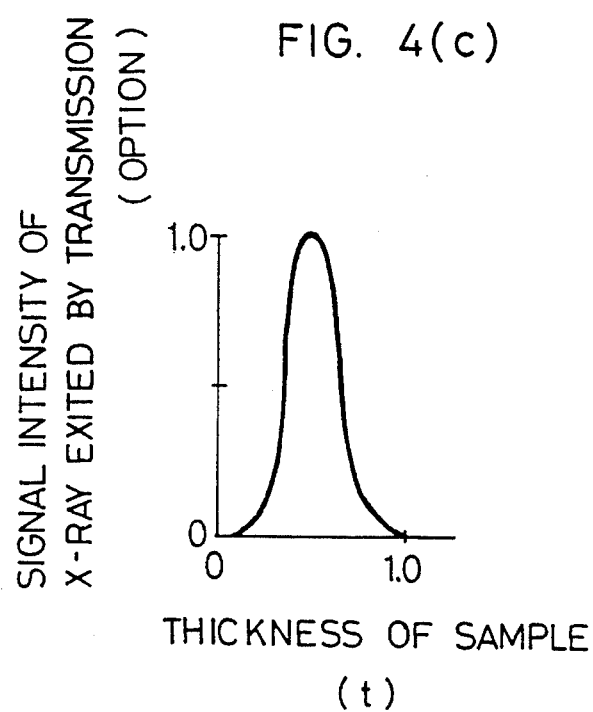

In contrast to the above, the excited X ray intensity due to scattered transmission electron is drawn like FIG. 4(c), because, the intensity of scattered transmission electron becomes maximum when the thickness of sample is not thinner enough, and the intensity decreases when the thickness of sample becomes more thinner.

By way of transmission electron or excited X ray by scattered transmission electron, too, thickness of thin film sample can be estimated, through measurement or calculation, beforehand, of the relation between the thickness of sample and intensity ratio between irradiated electron beam intensity and transmission electron intensity or between irradiated electron beam intensity and excited X ray by scattered transmission electron. That is why transmission electron or excited X ray by scattered transmission electron are also as best means for TEM sample making as reflection electron, since confirmation of thickness of sample can be done in thin film making process.

FIG. 5 exhibits the image of sample cross-section of which sample is processed through thin-film processing, by way of observation of signals specified. The images are different each other by element or crystalline structure, since reflection ratio or transmission ratio, of electron beam are different by element or crystalline structure. The bigger the atomic number of element is, the bigger the reflection electron intensity is. Therefore, the reflection electron image is as shown in FIG. 5(a), since the image of W wire 16 becomes brighter than those of, Al wire 15 or P-Si wire 17. In contrast to the above, the image by transmission electron is as shown in FIG. 5(b), since transmission electron density becomes smaller according to the smaller atom number element, and since even W wire 16 of the same thickness can not be transmitted by irradiated electron, although the thickness in case of Al wire 15 or P-Si wire 17 can be transmitted by it easily enough.

Since almost transmission electron in case of not thinner enough thickness of sample is scattered electron, X ray image which is mapped at the entrance turns to be FIG. 5(c), which shows the image of the element which constitutes the entrance and which is the image of excited X ray by scattered transmission electron.

Because X ray is emitted from the entrance element by way that such scattered transmission electron strikes the entrance (made of metal) of transmission electron detector at the bottom of sample. Moreover, the element analysis of very small portion located in specific place desired can easily be done, since X ray emitting area on thin film sample is very small. FIG. 5(d) shows the secondary electron image at this analysis above. By displaying those detected signal image(s) on single or multiple number of CRT, and by monitor-displaying the change in signal intensity, too, as shown in FIG. 4 in accordance with thin film processing by ion beam, such thin film processing of sample can easily be done down to the required size.

Since thin-film processing of sample and the on-going estimation of the thickness thereof can be done according to this invention, the apparatus and the method in this invention is the best for the thin-film processing of TEM sample which especially requires the observation and analysis of specific portion or position.

As explained hereinabove, this invention is the most suitable for TEM sample processing which requires the thickness confirmation and thin-film processing, of specific predetermined portion or position. Because, according to this invention, specific predetermined portion or position of sample can be thin film processed through etching with ion beam, the confirmation of processing position, processing shape, and cross-section, of sample and analysis at very sample portion or position can easily be done by way of, changing ion beam to electron beam, observing SEM image, or executing X ray analysis, if necessary in processing of ion beam etching above, and the thin film processed thickness of sample can be estimated by way of monitoring reflection electron, transmission electron or scattered transmission electron.

What is claimed is:

1. A focused charged beam apparatus comprising:
   a sample stage for holding a sample at a sample location;
   a focused ion-beam optics system for forming a focused ion beam, directing the focused ion beam along an ion beam axis, scanning a surface of the sample with the focused ion beam, and irradiating a predetermined area of the surface of the sample with the focused ion beam;
   a focused electron beam irradiation system for forming a focused electron beam, directing the focused electron beam along an electron beam axis which is perpendicular to the ion beam axis, and scanning and irradiating a surface of the sample with the focused electron beam; and
   a transmission electron detector disposed for detecting electrons of the focused electron beam which are transmitted through the sample at the sample location, said transmission electron detector being located so that the sample at the sample location is interposed between the focused electron beam which irradiates the sample and said transmission electron detector.

2. Apparatus as defined in claim 1 further comprising: a secondary electron detector for detecting secondary electrons emitted from the sample in response to irradiation by the focused electron beam.

3. Apparatus as defined in claim 2 wherein said secondary electron detector further detects secondary electrons emitted from the sample in response to irradiation by the focused ion beam.

4. A method for processing a sample for observation by transmission electron microscopy, comprising the steps of:
   irradiating a surface of the sample with a scanning focused ion beam having a beam axis so as to form a thin film on the surface;
   irradiating the thin film with a scanning focused electron beam having a beam axis perpendicular to the ion beam axis;
   detecting electrons which are transmitted through the thin film during irradiation with the focused electron beam; and
   monitoring the intensity of the detected electrons in order to determine the thickness of the thin film.

5. A method for processing a sample for observation by transmission electron microscopy, comprising the steps of:
   irradiating a surface of the sample with a scanning focused ion beam having a beam axis so as to form a thin film on the surface;
   irradiating the thin film with a scanning focused electron beam having a beam axis perpendicular to the ion beam axis;
   detecting secondary electrons emitted from the thin film in response to irradiation with the focused electron beam;
   monitoring the intensity of the detected secondary electrons in order to determine the thickness of the thin film; and
   determining the thickness of the thin film from the intensity of the detected secondary elections.

6. A method for processing a sample for observation by transmission electron microscopy, comprising the steps of:
   irradiating a surface of the sample with a scanning focused ion beam having a beam axis so as to form a thin film on the surface;
   irradiating the thin film with a scanning focused electron beam having a beam axis perpendicular to the ion beam axis;
   detecting X-rays emitted from the thin film in response to irradiation with the focused electron beam;
   monitoring the intensity of the detected X-rays in order to determine the thickness of the thin film; and
   determining the thickness of the thin film from the intensity of the detected X-rays.

* * * * *